(12) United States Patent
Serrano-Ojeda

(10) Patent No.: US 10,292,956 B2
(45) Date of Patent: May 21, 2019

(54) CANCER STARVATION THERAPY

(71) Applicant: Pedro Anastacio Serrano-Ojeda, San Juan, PR (US)

(72) Inventor: Pedro Anastacio Serrano-Ojeda, San Juan, PR (US)

(73) Assignee: Serbig Pharmaceutics Corp., Bayamon, PR (US)

( * ) Notice: Subject to any disclaimer, the term of this patent is extended or adjusted under 35 U.S.C. 154(b) by 0 days.

(21) Appl. No.: 14/860,204

(22) Filed: Sep. 21, 2015

(65) Prior Publication Data

US 2016/0058728 A1 Mar. 3, 2016

Related U.S. Application Data

(63) Continuation-in-part of application No. 12/552,116, filed on Sep. 1, 2009, now abandoned.

(51) Int. Cl.

| | | |
|---|---|---|
| A61K 31/07 | (2006.01) |
| A61K 31/14 | (2006.01) |
| A61K 31/19 | (2006.01) |
| A61K 31/51 | (2006.01) |
| A61K 33/06 | (2006.01) |
| A61K 33/18 | (2006.01) |
| A61K 36/28 | (2006.01) |
| A61K 39/00 | (2006.01) |
| A61K 31/122 | (2006.01) |
| A61K 31/194 | (2006.01) |
| A01N 43/00 | (2006.01) |
| A01N 43/46 | (2006.01) |
| A61K 31/55 | (2006.01) |
| A61K 31/198 | (2006.01) |
| A61K 31/28 | (2006.01) |
| A61N 5/10 | (2006.01) |
| A61N 5/02 | (2006.01) |
| A61K 41/00 | (2006.01) |
| C07F 1/00 | (2006.01) |
| A61K 47/54 | (2017.01) |
| A61K 31/197 | (2006.01) |
| A61K 31/355 | (2006.01) |
| A61K 31/375 | (2006.01) |
| A61K 31/455 | (2006.01) |
| A61K 31/519 | (2006.01) |
| A61K 31/525 | (2006.01) |
| A61K 31/555 | (2006.01) |
| A61K 31/593 | (2006.01) |
| A61K 31/714 | (2006.01) |
| A61K 31/4415 | (2006.01) |

(52) U.S. Cl.
CPC ............ *A61K 31/198* (2013.01); *A61K 31/28* (2013.01); *A61K 41/0038* (2013.01); *A61K 47/542* (2017.08); *A61N 5/02* (2013.01); *A61N 5/10* (2013.01); *C07F 1/00* (2013.01); *A61N 2005/109* (2013.01); *A61N 2005/1087* (2013.01)

(58) Field of Classification Search
None
See application file for complete search history.

(56) References Cited

U.S. PATENT DOCUMENTS

| | | |
|---|---|---|
| 2004/0181114 A1 | 9/2004 | Hainfeld et al. |
| 2006/0233744 A1 | 10/2006 | Shultz et al. |
| 2009/0130154 A1 | 5/2009 | Gupta |
| 2009/0169591 A1 | 7/2009 | Kaul et al. |
| 2011/0054019 A1 | 3/2011 | Serrano Ojeda |
| 2012/0263645 A1 | 10/2012 | Watanabe et al. |
| 2013/0177523 A1 | 7/2013 | Ghandehari et al. |

FOREIGN PATENT DOCUMENTS

WO    WO 2005072061 A2 * 8/2005 ....... A61K 47/48038

OTHER PUBLICATIONS

Ellis et al.*
African Regional Intellectual Property Organization Official Action dated Dec. 5, 2014 in corresponding African patent application AR/P/2012/006202.
Rahman et al. Enhancement of radiation effects by gold nanoparticles for superficial radiation therapy. Nanomedicine. Jun. 2009; 5(2): 136-142.
Medina. Glutamine and Cancer. J. Nutr. Sep. 1, 2001 vol. 131 No. 9.
International Search Report and Written Opinion for PCT/US2016/052603 dated Dec. 2, 2016.
Kadri Valter, Lian Chen, Björn Kruspig, Polina Maximchik, Hengmin Cui, Boris Zhivotovsky, Vladimir Gogvadze. Contrasting effects of glutamine deprivation on apoptosis induced by conventionally used anticancer drugs. Biochimica et Biophysica Ada 1864 (2017) 498-506.
Ahmad A.Cluntun, Michael J.Lukey, Richard A.Cerione, and JasonW. Locasale. Glutamine Metabolism in Cancer: Understanding the Heterogeneity. Trends in Cancer 2017, 01, 005, 1-12.
Brown AL, Kai MP, DuRoss AN, Sahay G, Sun C. Biodistribution and Toxicity of Micellar Platinum Nanoparticles in Mice via Intravenous Administration. Nanomaterials (Basel). Jun. 2018; 8(6): 410.
Xiao-Qun Ye1, Qi Li1, Guang-Hui Wang, Fen-Fen Sun, Gui-Jun Huang, Xiu-Wu Bian, Shi-Cang Yu, and Gui-Sheng Qian. Mitochondrial and energy metabolism-related properties as novel indicators of lung cancer stem cells. Int. J. Cancer: 129, 820-831 (2011).

(Continued)

Primary Examiner — Layla Soroush
(74) Attorney, Agent, or Firm — Hogan Lovells US LLP

(57) ABSTRACT

The present invention is a glutamine compound having a high Z element attached via a ligand, which enters the mitochondrion and is subsequently exposed to ionizing radiation. When exposed to ionizing radiation, the present invention damages mitochondrial (as well as other) substructures such as mtDNA, the outer membrane, the inner membrane, cristae, ribosomes, etc., and causes the effective destruction of such mitochondrion. Tumorigenic cells without mitochondria cannot produce the energy they need to subsist and replicate, effectively starving them of energy and causing their destruction.

1 Claim, 7 Drawing Sheets

(56) References Cited

OTHER PUBLICATIONS

Yao-An Shen, Chia-Yu Wang, Yi-Tao Hsieh, Yann-Jang and Yau-Huei. Metabolic reprogramming orchestrates cancer stem cell properties in nasopharyngeal carcinoma. Cell Cycle 14:1, 86-98; Jan. 1, 2015.
Joana Peixoto and Jorge Lima. Metabolic traits of cancer stem cells. Disease Models & Mechanisms (2018) 11.
Gregory LaMonte, Xiaohu Tang, Julia Ling-Yu Chen. Acidosis induces reprogramming of cellular metabolism to mitigate oxidative stress. Cancer & Metabolism 2013, 1:23.
Chih-Hua Yeh, Gigin Lin, Jiun-Jie Wang, Chien-Yu Lin, Shang-Yueh Tsai, Yu-Chun Lin, Yi-Ming Wu, Sheung-Fat Ko, Hung-Ming Wang, Sheng-Chieh Chan, Tzu-Chen Yen, Chun-Ta Liao and Shu-Hang Ng. Predictive value of 1H MR spectroscopy and 18F-FDG PET/CT for local control of advanced oropharyngeal and hypopharyngeal squamous cell carcinoma receiving chemoradiotherapy: a prospective study. Oncotarget, 2017, vol. 8, (No. 70), pp. 115513-115525.
Final Office Action dated Dec. 17, 2018 in U.S. Appl. No. 15/449,529, filed Mar. 3, 2017.

\* cited by examiner $$K_c = \int \frac{\Psi}{\rho}(\tau_{tr} + \sigma_{tr} + \kappa_{tr})(1-g)dE$$

Figure 1

$$\sigma_{tr} = 2\pi r_0^2 \frac{N_A Z \rho}{A_w}\left[\frac{2\left(1+\frac{h\upsilon}{m_0 c^2}\right)^2}{\left(\frac{h\upsilon}{m_0 c^2}\right)^2\left(1+2\frac{h\upsilon}{m_0 c^2}\right)} - \frac{1+3\frac{h\upsilon}{m_0 c^2}}{\left(1+2\frac{h\upsilon}{m_0 c^2}\right)^2}\right.$$
$$\frac{\left(1+\frac{h\upsilon}{m_0 c^2}\right)\left(2\left(\frac{h\upsilon}{m_0 c^2}\right)^2 - 2\frac{h\upsilon}{m_0 c^2}-1\right)}{\left(\frac{h\upsilon}{m_0 c^2}\right)^2\left(1+2\frac{h\upsilon}{m_0 c^2}\right)^2} - \frac{4\left(\frac{h\upsilon}{m_0 c^2}\right)^2}{3\left(1+2\frac{h\upsilon}{m_0 c^2}\right)^3}$$
$$\left. -\left(\frac{1+\frac{h\upsilon}{m_0 c^2}}{\left(\frac{h\upsilon}{m_0 c^2}\right)^3} - \frac{1}{2\frac{h\upsilon}{m_0 c^2}} + \frac{1}{2\left(\frac{h\upsilon}{m_0 c^2}\right)^3}\right)\ln\left(1+2\frac{h\upsilon}{m_0 c^2}\right)\right]$$

Figure 2

$$\left(\frac{dT}{dx}\right)_c = 2\pi r_0^2 \frac{N_A Z \rho}{A_w}\left[\frac{m_0 c^2}{1-\left(\frac{1}{T/m_0 c^2+1}\right)^2}\right]\left[\ln\left(\frac{(T/m_0 c^2)^2(T/m_0 c^2+2)}{2(I/m_0 c^2)^2}\right)+\left(\frac{1}{T/m_0 c^2+1}\right)^2\right.$$
$$\left. +\frac{(T/m_0 c^2)^2/8 - (2\,T/m_0 c^2+1)\ln 2}{(T/m_0 c^2+1)^2} - \delta - \frac{2C}{Z}\right]$$

Figure 3

$$\left(\frac{dT}{dx}\right)_r = \frac{r_0^2}{137}\cdot\frac{N_A Z^2 \rho}{A_w}(T+m_0 c^2)\bar{B}_r$$

Figure 4

$$g = \frac{\int_0^{T_{max}}\left[\frac{1}{T_0}\int_0^{T_0}\frac{(dT/dx)_r}{(dT/dx)_r+(dT/dx)_c}dT\right]\left[\left(\frac{d\tau}{dT_0}\right)+\left(\frac{d\sigma}{dT_0}\right)+\left(\frac{d\kappa}{dT_0}\right)\right]dT_0}{\int_0^{T_{max}}\left[\left(\frac{d\tau}{dT_0}\right)+\left(\frac{d\sigma}{dT_0}\right)+\left(\frac{d\kappa}{dT_0}\right)\right]dT_0}$$

Figure 5

$$A = \frac{\text{mean charged particle fluence from High Z analogue}}{\text{mean charged particle fluence from molecule}}$$

$$A = \frac{({_a\tau_{tr}^Z} + {_a\sigma_{tr}^Z} + {_a\kappa_{tr}^Z})}{({_a\tau_{tr}^C} + {_a\sigma_{tr}^C} + {_a\kappa_{tr}^C})} \cdot \frac{(1-g^Z)}{(1-g^C)}$$

$$\frac{Z}{A}\ln I = \sum_i [f_{Z_i}(Z/A)_i \ln I_i]$$

$$\frac{Z}{A}\delta = \sum_i f_{Z_i}(Z/A)_i \delta_i$$

Glutamine

Formula I     Formula II     Formula III     Formula IV     Formula V

X = O, S, NH
linker = $(CH_2)_n$-X, $[(CH_2CH_2)_{m'}X]_n$
Z = group with high Z-element Examples of Formula I

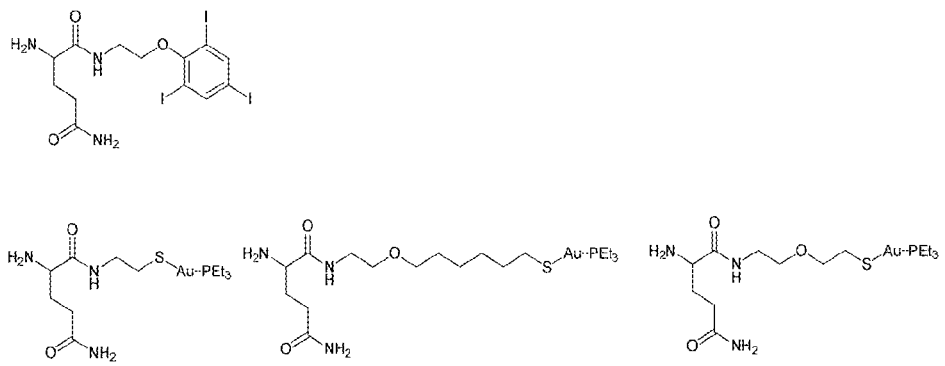
Figure 17
Examples of Formula II
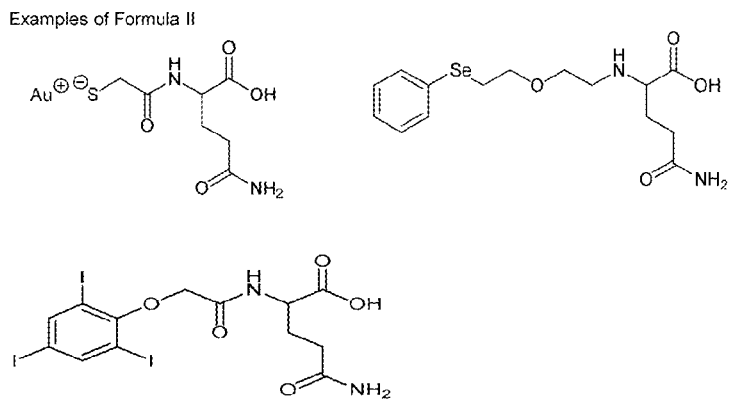
Figure 18
Examples of Formula III
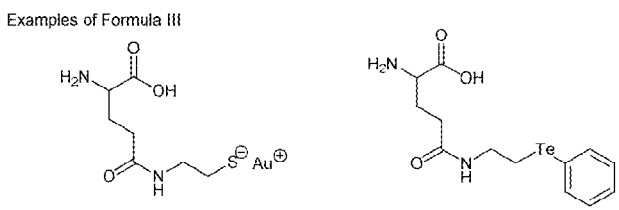
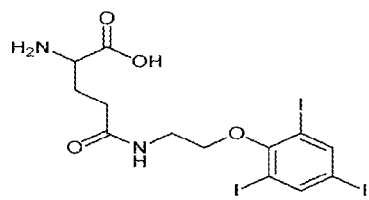

Examples of Formula IV

Examples of Formula V

CANCER STARVATION THERAPY

RELATED APPLICATIONS

This application is a continuation-in-part of U.S. Ser. No. 12/552,116, which was filed on Sep. 1, 2009, which is incorporated herein in its entirety.

BACKGROUND OF THE INVENTION

Field of the Invention

The present invention describes a method for the ablation of targeted tissue or cells via the administration of glutamine analogues containing platinum, iron, and/or other high Z elements and subsequently exposing such tissue or cells to high energy radiation, including, but not limited to, x-rays, gamma rays, microwaves, alpha particles, protons, and neutrons. More specifically, the present invention describes a method for targeting the mitochondria of the aforementioned tissue or cells for destruction, thereby starving such cells of the energy they require to proliferate.

Background

Radiation therapy is usually defined as the use of high-energy radiation from x-rays, gamma rays, neutrons, protons, and other sources to kill cancer cells and shrink tumors. Radiation may come from a machine outside the body also called external-beam radiation therapy, or it may come from radioactive material placed in the body near cancer cells also called internal radiation therapy.

Radiation therapy, however, has its limitations. The ionizing radiation used to ablate unwanted tissue can cause damage to surrounding healthy tissue, or may not be effective against the target tissue due to conditions such as hypoxia which makes the targeted cells radioresistent or cells being in a part of the mitotic cycle where they are not as sensitive to the effects of such radiation. Much study and effort has been expended developing compounds and techniques to enhance the effectiveness of radiation therapy and limit the damage to healthy, non-targeted tissue.

Radiosensitizers are drugs created to enhance the effectiveness of radiation therapy by making tumorigenic cells more susceptible to the effects of radiation. One class of radiosensitezers, known as halogenated pyrimidines, accomplishes this enhancing effect by directly making DNA more susceptible to damage from radiation. This class of radiosensitizers works by incorporating halogenated pyrimidines directly into the DNA chain in substitution of thymidine. This substitution weakens the DNA chain and makes cells more susceptible to radiation and ultraviolet light. Another class of radiosensitizers functions by fast ionization/deexcitation processes and the strong emission of secondary electrons. Yet another class of radiosensitizers, known as hypoxic-cell sensitizers, increase the radiation sensitivity of tumorigenic cells deficient in molecular oxygen.

The radiosensitizing effects of these drugs are believed to aid the ionizing radiation by augmenting the latter's ability to damage nuclear DNA in creating strand breaks that are not repairable, therefore triggering apoptosis. It has also been theorized that the drug cisplatin, a chemotherapeutic drug that is known to have radio sensitizing properties, may cause damage to mitochondrial structures.

Further, cellular respiration is the set of metabolic processes by which biochemical energy from nutrients is converted to energy in the form of andostein triphosphate ("ATP"). During normal aerobic cellular respiration, one molecule of glucose, the most abundant nutrient in mammalian serum, is converted to two molecules of pyruvate and two net molecules of ATP. This process is known as glycolysis. The pyruvate is then further broken down in order to release a theoretical yield of 36-38 molecules of ATP.

The mitochondria, which plays an important part in the aerobic cellular respiration process, are spherical or elongated organelle in the cytoplasm of nearly all eukaryotic cells, containing genetic material and many enzymes important for cell metabolism, including those responsible for the conversion of food to usable energy. Mitochondria provide the energy a cell needs to move, divide, produce secretory products, contract—in short, they are the power centers of the cell. They are about the size of bacteria but may have different shapes depending on the cell type.

Mitochondria are membrane-bound organelles, and like the nucleus have a double membrane. The outer membrane is fairly smooth; the inner membrane is highly convoluted, forming folds called cristae. The cristae greatly increase the inner membrane's surface area, and it is here that mitochondrial electron transport occurs.

The elaborate structure of a mitochondrion is very important to the functioning of the organelle. Two specialized membranes encircle each mitochondrion present in a cell, dividing the organelle into a narrow intermembrane space and a much larger internal matrix, each of which contains highly specialized proteins. The outer membrane of a mitochondrion contains many channels formed by the protein porin and acts like a sieve, filtering out molecules that are too big. Similarly, the inner membrane, which is highly convoluted so that a large number of infoldings called cristae are formed, also allows only certain molecules to pass through it and is much more selective than the outer membrane. To make certain that only those materials essential to the matrix are allowed into it, the inner membrane utilizes a group of transport proteins that will only transport the correct molecules. Together, the various compartments of a mitochondrion are able to work in harmony to generate ATP in a complex multi-step process.

The mitochondrion is different from most other organelles because it has its own circular DNA (similar to the DNA of prokaryotes) and reproduces independently of the cell in which it is found; an apparent case of endosymbiosis. Mitochondrial DNA is localized to the matrix, which also contains a host of enzymes, as well as ribosomes for protein synthesis. Many of the critical metabolic steps of cellular respiration are catalyzed by enzymes that are able to diffuse through the mitochondrial matrix. The other proteins involved in respiration, including the enzyme that generates ATP, are embedded within the mitochondrial inner membrane. Infolding of the cristae dramatically increases the surface area available for hosting the enzymes responsible for cellular respiration.

Human mitochondria contain 5 to 10 identical, circular molecules of DNA. Each molecule contains 16,569 base pairs that encode 37 genes including ribosomal RNA (rRNA), transfer RNA (tRNA), and 13 polypeptides. The 13 proteins are an important part of the protein complexes in the inner mitochondrial membrane, forming part of complexes I, III, IV, and V. These protein complexes also dependent upon proteins encoded by nuclear DNA which are synthesized in the cytosol and imported into the mitochondria.

In the absence oxygen, a hypoxic cell can still generate energy through glycolysis and generate two net molecules of ATP. However, under such hypoxic conditions, the resulting pyruvate is not transported into the mitochondria for further processing, but rather remains in the cytoplasm where it is converted to lactate by lactic acid fermentation and expelled from the cell. This process is known as anaerobic respiration.

Interestingly, it has been observed for some time that even in the presence of oxygen, rapidly proliferating tumorgenic cells have a preference for inefficient anaerobic respiration and therefore utilize an abnormally high amount of glucose. This is known as aerobic glycolysis, or the Warburg Effect, named after Otto Heinrich Warburg, who made the discovery in 1926. Various theories have been put forth to account for this effect, among which is that glucose degradation provides cells with intermediaries used in a variety of biosynthetic pathways. It is therefore theorized that tumor cells maintain robust glycolysis in order to keep a ready supply of such intermediaries.

Glucose is not however, the only compound to be consumed at highly elevated levels by proliferating cancerous cells. These cells also use copious amounts of glutamine relative to non-tumorigenic cells. Glutamine is a non-essential amino acid present abundantly throughout the body and is involved in many metabolic processes. It is synthesized from glutamic acid and ammonia. It is the principal carrier of nitrogen in the body and is an important energy source for many cells.

In cancerous cells, the TCA cycle is truncated because such cells use carbon from the cycle for biosynthetic purposes. Citrate therefore is unlikely to cycle all the way back around and regenerate oxaloacetic acid ("OAA"). Tumors solve the problem of the need to regenerate OAA—and also generate much of the energy they need to proliferate—by oxidizing large amounts of the amino acid glutamine and incorporating it into the truncated TCA cycle. In tumorigenic cells, the truncated TCA cycle incorporates glutamine and pyruvate supplied by the phosphorylation of glucose to generate energy and create precursors for biosynthetic pathways.

The phenomenon of significantly increased glutamine utilization in tumorigenic cells has been previously studied as a potential pathway by which therapeutic anti-cancer drugs may act. The glutamine analogues L-[alpha S,5S]-alpha-amino-3-chloro-4,5-dihydro-5-isoxazoleacetic acid (acivicin) and 6-diazo-5-oxo-L-norleucine (DON) are known to possess cytotoxic activity against a wide variety of tumors. These drugs are thought to function by inhibiting mitochondrial enzymatic activity. However, their usefulness as therapies for humans has been limited due to their high toxicity.

To date, there has been no drug specifically designed as a radiosensitizer that targets the mitochondria of tumorigenic tissue and cells for destruction.

Physical Aspects of High-Z Materials and Charged Particle Amplification

The following discusses the effects of high-Z materials on the atomic (picometer, or 1E-12 meter) scale, by comparing the individual interaction rates of different materials when exposed to a fluence of charged particles and gamma- or x-ray photons. Furthermore, in the context of therapeutic radiation, the energy deposition models provided herein for the orthovoltage and megavoltage energy ranges are 2E5 to 1.8E7 eV, or 3.2E-14 to 2.88E-12 J.

For therapeutic irradiation, tissue is exposed to a calibrated beam of electrons or photons. Photons indirectly interact with matter through coherent, photoelectric, Compton, or pair production collisions. Coherent scattering results in no energy deposition, and will not be discussed further. The remaining collisions result in the emission or ejection of electrons. The scattered electrons further deposit energy by directly interacting with nearby atoms in collisional or radiative type events, potentially ejecting additional electrons (δ rays). The total amount of kinetic energy per unit mass lost from the photons and δ (delta) rays in non-radiative processes is referred to as collision kerma, or $K_c$. The units are typically given in J/kg, or Gy. In the presence of charged particle equilibrium, the total amount of absorbed dose is equal to the collision kerma. In surrounding matter, the dose deposition process results in the generation of free electrons and ions which can damage the DNA or other cellular structures; in the case of the present invention, the mitochondria. Collision kerma can be calculated directly from the collision probabilities (or cross sections) of each interaction using the formula as in FIG. 1, where ψ (psi) refers to the incident photon energy fluence in $J/cm^2$, P is the material density in $g/cm^3$, g is the average fraction of secondary electron energy lost to radiative processes. The values $T_{tr}$, $\sigma_{tr}$, and $K_{tr}$, refer to the energy transfer cross sections, in $cm^{-1}$, for photoelectric, Compton, and pair production interactions, respectively.

For incident photon energies of 0.5 to 5 MeV on almost all materials, the Compton cross section dominates the above equation; that is, $\sigma_{tr} > T_{tr}$, $K_{tr}$. The cross section for Compton interactions has been rigorously modeled by Klein and Nishina (Evans, 1955), as shown in FIG. 2, who defined the following statement for $\sigma_{tr}$, where $r_0$ refers to the classical electron radius $e^2/m_0c^2 = 2.818 \times 10^{-13}$ cm, $N_A = 6.022 \times 10^{23}$ mole-1 is Avagadro's constant, Z is the number of electrons per atom, $A_w$, is the atomic weight in grams, $h = 6.626 \times 10^{-34}$ is Planck's constant in J-s, v is the frequency of incident radiation in $cm^{-1}$, $m_0 = 0.91095 \times 10^{-30}$ kg is the rest mass of an electron, and $c = 2.9979 \times 10^{10}$ cm/sec is the speed of light.

For incident electrons with energy T (in J), the expectation value for rate of energy loss due to collisional events through a linear distance x (in cm) can be described by the collision stopping power of a material, or $(dT/dx)_c$. FIG. 3 defines the collision stopping power for electrons adjusted for the polarization effect and shell correction, where 1 is the mean ionization/excitation potential (Berger & Seltzer, 1983) of the material in J, δ is the polarization correction parameter (Stermheimer, 1952), and c is the shell correction parameter (Bichsel, 1968).

Similarly, the expectation value for energy loss due to radiative events, i.e. bremsstrahlung, is described by the radiative stopping power $(dT/dX)_r$, and is shown in FIG. 4. The value $B_r$ is defined by Bethe and Heitler (Evans, 1955), and carries a slight dependence on Z and T.

The radiation yield, therefore, is simply the mean ratio of energy loss to radiative processes relative to the total rate of energy loss over all initial electron energies and as each electron loses energy. FIG. 5 shows the radiation yield formula, where $T_{max}$ refers to the maximum initial electron energy.

In order to achieve an increased dosimetric effect from external ionizing radiation, targeted molecules located around a biological target can be replaced with appropriate analogues that contain one or more high-Z elements. An important quantifier for this effect can be defined as the relative increase in the expectation value of charged particle fluence created by the high-Z analogue over that of the original molecule. This value, herein referred to as the amount of charged particle amplification A, is shown in FIG. 6.

As defined above, the value of A is dependent on the type of molecule used for high-Z implementation. Furthermore, the effects of molecular binding on each high-Z atom will modify slightly the above equations that define the interaction rates. That said, numerical values for A can be estimated and quantified for each individual high-Z elemental substitution performed in a molecule using the above formulas. For photon interactions, the increase in charged particle fluence is simply the ratio of energy transfer interaction probabilities (the subscript a is used to denote these probabilities in units of $cm^2$/atom). Similarly, the reduction in fluence may be estimated for electron interactions by comparing the ratio of energy lost to radiative processes. FIG. 7 presents a formula wherein these results compete to formulate A, where the superscript z refers to the interaction cross sections for the high-Z material, while c refers to the element substituted (considered a carbon atom).

Values for A have been plotted in FIG. 8 for atomic numbers $Z=1$ through 90, where carbon ($Z=6$) is used as the reference, using published energy absorption cross sections (Seltzer, 1993). Data for three incident photon energies has been given: a monoenergetic 500 keV theoretical beam, and polyenergetic 6 MV and 18 MV beams typically found on a modern therapeutic linear accelerator. As an example, three gold atoms ($Z=79$) would yield a factor of $17\times3=51:1$ higher fluence rate than three carbon atoms present in the same molecule for a 6 MV photon beam. The same replacement would yield a factor of 136:1 and 82:1 for 500 keV photons and an 18 MV beam, respectively. In order to apply this value to the entire molecule, A can be expanded to include the atomic fractions $f_1$, $f_2$ of each element with atomic number $Z_1$, $Z_2$, etc. present in the compound. In addition, Bragg's rule can be applied to estimate the mean ionization potential and polarization correction, as shown in FIG. 9.

SUMMARY OF THE INVENTION

The present invention helps to overcome the limitations of radiation therapy as disclosed above, by providing a radiosensitizing glutamine analogue containing platinum, iron, and/or other high Z elements, which when exposed to x-rays or other ionizing or high energy radiation such as gamma rays, alpha particles, protons, neutrons, or fast ions, causes the destruction of mitochondrial and other structures of targeted tissue and cells.

Another object of the present invention is the destruction of the mitochondria, wherein said destruction effectively denies energy and substrates necessary for proliferation for cancerous cells.

Another object of the present invention is to destroy mitochondrial structures of target cells, thereby rendering the mitochondria nonfunctional and starving the cell of the energy and substrates necessary for its survival.

Another object of the present invention is to interact with the mitochondria instead of the DNA. Radiation therapy traditionally targets nuclear DNA for destruction. However, in proliferating cells, unless such cell is undergoing mitotic division the double helix strand of nDNA has not condensed into a chromosome and is therefore not susceptible to the same irreparable damage as if the cell were in mitosis. The current invention does not primarily seek to destroy nuclear DNA, although nDNA damage of target tissue may result and would be desirable.

Yet another object of the present invention is to provide a radiosensitizing compound where one or more atoms, functional groups, or substructures of glutamine have been replaced with at least one or more high Z elements.

The invention consists of platinum, iron, and/or other high Z elements located at the center of the glutamine analogue, thereby replacing one or multiple carbons. Further the invention provides of high Z elements being attached via a side chain or ligand to the glutamine analogue. The side chain or ligand may be a linker of (CH2)n-X, or [(CH2CH2)mX]n where X=O, S, or NH.

Irrespective of the embodiment, the invention may be administered by any standard method, including, but not limited to, intravenously, intra-arterially, orally, or direct injection into targeted tissue in vivo or in vitro.

High Z elements suitable for inclusion in the invention are those with a Z value of at least 22, and include, but are not limited to, platinum (Z=78), vanadium (Z=23), iron (Z=26), cobalt (Z=27), copper (Z=29), molybdenum (Z=42), palladium (Z=46), silver (Z=47), tin (Z=50), tantalum (Z=73), gadolinium (Z=64), dysprosium (Z=66), holmium (Z=67), hafnium (Z=72), tungsten (Z=74), rhenium (Z=75), osmium (Z=76), iridium (Z=77), gold (Z=79), thallium (Z=81), lead (Z=82), bismuth (Z=83), and uranium (Z=92).

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings which are incorporated herein constitute part of the specifications and illustrate the preferred embodiment of the invention.

FIG. 1 shows a collision probability equation.

FIG. 2 shows a Compton interaction model.

FIG. 3 shows the collision stopping power equation for electrons.

FIG. 4 shows a radiative stopping power equation.

FIG. 5 shows a radiation yield equation.

FIG. 17 provides examples of Formula II.

FIG. 18 provides examples of Formula III.

DESCRIPTION OF THE INVENTION

The present invention is directed to a glutamine analogue composition, wherein said composition is design to be exposed and enter the mitochondrion, more particularly the mitochondria of not-healthy cells, such as but not limited to cancer cells. Subsequently the not-healthy cells become a target, wherein said targeted cells are exposed to ionizing radiation. When exposed to ionizing radiation, the present composition, having metallic particles, reacts in such way that damages mitochondrial (as well as other) substructures such as mtDNA, the outer membrane, the inner membrane, cristae, ribosomes, etc., and causes the effective destruction of such mitochondrion. The destruction of the mitochondria starts the programmed cell death of Tumorigenic cells for the reason that without mitochondria Tumorigenic cells cannot produce the energy they need to subsist and replicate, effectively starving mitochondria damaged cells of energy and causing their destruction.

The invention provides a glutamine-ligand-high Z element compound for treating tumorigenic cells in combination with a high energy radiation. The glutamine-ligand-high Z element compound is selected from the group of compounds having the Formula I, II, III, IV and IV (as provided in FIG. 15). This molecule (has been termed by the inventor as the "Cancer Starvation Molecule" and the cancer treatment therapies using these compounds (along with high energy radiation) has been termed Cancer Starvation Therapy."

The Cancer Starvation Molecule was morphed from the convergence of observation of simple facts, starting by simple observation of radiation toxicity for head and neck patients, tumor microenvironment and resistance to conventional therapies, to more elaborate ideas. To date, all novel cancer approaches have helped strengthen the idea that treatments directed to the tumor metabolic pathways are the next step that could help us win the battle against cancer.

Figure 21:
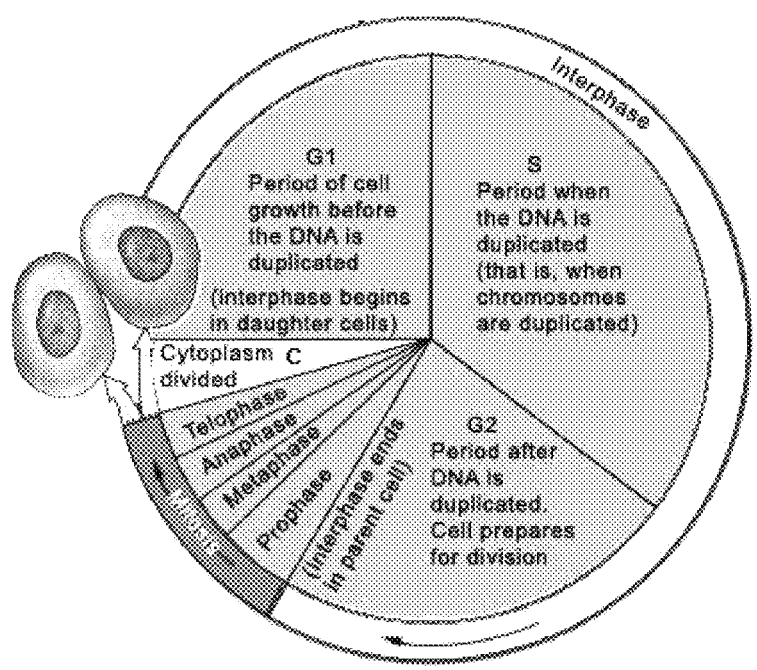
FIG. 21 provides a diagram of the cell cycle.

The fact is that radiation therapy mainly works by damaging the DNA, which is more vulnerable in the parts of the cancer cell cycle that are also the shortest, specifically G2 and Mitosis. See FIG. 21. Even this handicap has not deterred scientists from making big strides in the battle against cancer, but there is a whole ocean of possibilities in the rest of the cancer cell cycle where conventional therapies are weak. Within the big ocean of possibilities is where the therapeutic ratio (increase cancer killing capacity with less damage possible to the patient) can improve exponentially with a Cancer Starvation Molecule (CSM) and Cancer Starvation Therapy (CST).

Cancer Starvation Molecule is an organometallic molecule nonexistent in nature and capable of crossing the blood brain barrier. It was designed to enter inside the cancer cell mitochondria with predilection for tissue with low oxygen concentration (hypoxic tissue) and to be activated by a physical reaction or radiation. Therefore it is designed to work at the parts of the cancer cell cycle were chemotherapy and radiation therapy notoriously, are known to fail.

It is believed that CSM and CST is suited for treating tumor culture cells like Glioblastoma multiforme (GBM). GBM are tumors that arise from glial cells or brain supporting cells, characterized by an impressive growth rate and high lethality. The landmarks that define GBM as a resistant disease reside in the fact that this tumor microenvironment is highly associated with low oxygen concentrations or hypoxia and that the tumor extends beyond what is visible by the currently available diagnostic technologies.

Tumors in hypoxic environments survived by changing their metabolism from aerobic to anaerobic, which are associated by an increased presence of lactate and increased consumption of glutamine. CSM is an organometallic composed of glutamine for selective transport of a heavy metal that is the source use to increase scattered radiation inside the cancer cell mitochondria. Hypoxic microenvironment is a harsh environment, also blamed to induce the formation of cancer stem cells or cancer immortal cells. The fact that these cancer stem cells are fast dividing cells in an environment notoriously resistant to conventional therapy is what makes it a perfect target for CST.

In the past therapies have attempted to conquer the battle against GBM through brute force, by increasing the radiation dose to a better defined target using Stereotactic Radio Surgery (SRS), Neutron therapy and Proton therapy. All these approaches failed because they cannot treat what cannot be seen by the available radiologic technologies. GBM is well known to be present 2-3 cm beyond what is the radiographically visible disease and using brute force therapies could kill more disease but also kills the patient. CST is designed as a Trojan's horse to be trapped by the cancer cell at the mitochondria, or the cell power house and be activated via conventional radiation therapy. By selectively damaging or even destroying the cancer cells mitochondria we cripple the cancer cell capacity to heal sub-lethal damage cause by conventional therapies, leading to damage similar to the brute force technologies but in a space that is controlled by the tumor itself.

Other cancers that could benefit for Cancer Starvation Therapy include lung cancer, head and neck cancer, melanoma, rectal cancer, pancreatic cancer, esophageal cancer, cervical cancer and bladder cancers among many others.

In the oncology arena lung cancer is the number one killer in developed countries. Tumor control is limited by disease volume, disease location, patient's performance status and radiation treatment doses. Local treatment failure is a major pattern of failure and although the cancer starvation molecule does not distinguish between cancers of glandular or epidermal origin, it can easily distinguish between normal and abnormal cells and could potentially be used for treatment of patients with few metastasis or oligo metastasis. This approach can take us closer to make cancer a chronic disease.

For patients with head and neck cancers local failure leads to permanent surgical mutilation. Imagine that you or someone you love losses their tongue and now they cannot verbalize their thoughts and cannot swallow food, or the ones that loss the larynx and now even bathing become a very risky activity.

Melanomas are known to be highly resistant to radiation because the melanoma cancer cells are known to contain high levels of antioxidants. With CST, melanoma will not only meet its match but very importantly the dramatic hike in the cost of melanoma medical care can be reduced. New melanoma medications can be as expensive as $300,000 a year, and yet they still are only a palliative approach. Our economically crumbling medical system cannot tolerate this nonsense. CST is about killing cancer stem cells and is about getting closer to achieve the abscopal effect.

For some years there have been a trend to treat rectal cancers with chemoradiation and then to delay definite surgery until there is evidence of local failure. When we analyze the percentage of rectal cancer patients were surgery can be left out of the curative approach, then is easy to realize that is about the same percentage of patients anticipated to achieve a complete pathological response with preoperative chemoradiation. Having a permanent colostomy is deleterious to the patient quality of life and local progression of disease leads to metastasis and death. CST can easily double or triple a pathological complete response for patients treated with preoperative chemoradiation, leading to a decrease utilization of surgery, decrease medical care cost and a more social and psychologically empowered patient, more willing to return to the labor force and more willing to live with purpose.

Having a pancreatic cancer diagnosis is very much consonant with a death sentence. Imagine that local and regional recurrence after successful surgery could be as high as 90%. Many other malignancies could be treated using the principles above described.

Figures 6, 7, 8, 9:
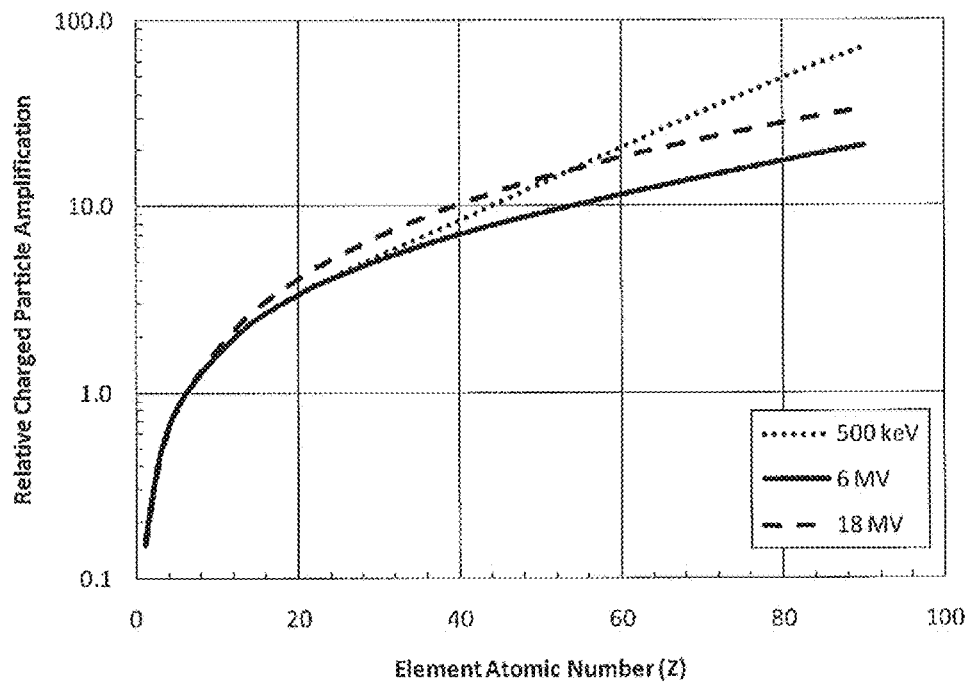
FIG. 6 shows the amount of charged particle amplification formula.
FIG. 7 shows relative amount of charged particle amplification formula when binding high Z-atoms.
FIG. 8 shows plotted values of FIG. 7 equation for different values of Z.
FIG. 9 shows an equation to estimate the mean of ionization potential and polarization correction.
Figure 10:
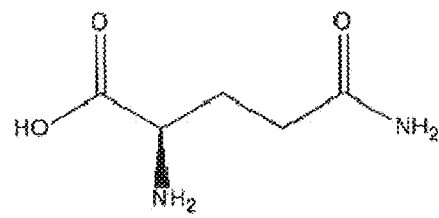
FIG. 10 shows the structure of glutamine, chemical formula $C_5H_{10}N_2O_3$.

FIG. 10 shows glutamine, wherein said glutamine is composed of a chain of three carbon atoms, Z=6, attached on either end to an additional atom of carbon. The present composition as mentioned consists in the replacement the core carbon atoms with high Z elements, such as gold atoms, Z=79. FIGS. 11-13 disclose several embodiments for the present invention. The present composition is generated, for example by replacing the carbon atoms. Further the present composition acts as a glutamine analogue compound that accesses the mitochondria. However due to the replacement of glutamine atoms for other high Z elements, such as but not limited to gold or copper, the properties of the element change providing a composition susceptible to radiation, as mentioned before.

Figure 11A:
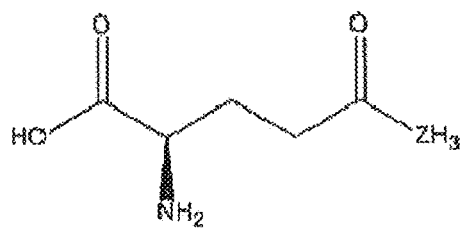
FIG. 11a-11b shows a structural analogue of present invention with single replacement.

FIG. 11(a), as an example, shows a first generic embodiment of the present invention compound wherein the structural analogue of glutamine, more particularly the amine functional group $NH_2$ is replaced with a high z element, and in this generic case, three Hydrogen atoms. The Nitrogen atom may also be replaced with any high z element that would require 2 (or any number) hydrogen atoms to bind with it, in which case such generic substitution would take the form $ZH_2$, where Z is any high z element as previously defined. Such general first embodiment is denoted with the generic chemical formula $C_5H_{11}ZNO_3$.

Figure 11B:
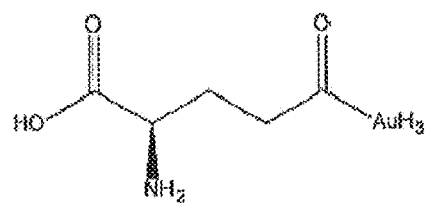

FIG. 11b provides a more specific embodiment of the first general embodiment presented in FIG. 11a above. As disclosed above the first embodiment consists of a structural analogue of glutamine where the amine functional group $NH_2$ is replaced with a high z element and three Hydrogen atoms such as $AuH_3$. The chemical formula for this specific compound is $C_5H_{11}AuNO_3$.

Figure 12A:
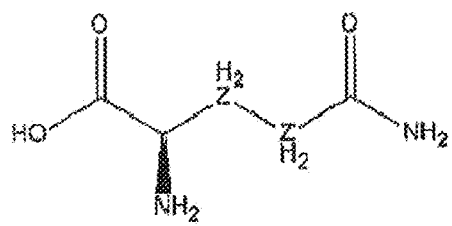
FIG. 12a-12b shows a structural analogue of present invention with 2 carbon replacement.

FIG. 12a, as an example, shows an second embodiment of the present invention, wherein a structural analogue of glutamine, more particularly two carbon atoms are replaced with high z elements. Z is any high z element as previously defined, wherein said general second embodiment is denoted with the generic chemical formula $C_3H_{10}Z_2N_2O_3$.

Figure 12B:
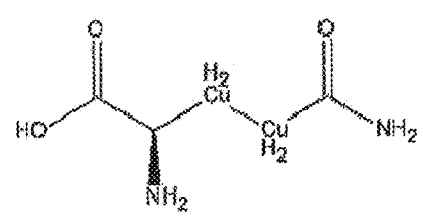

FIG. 12b provides a more specific second embodiment of the general embodiment presented in FIG. 12a above. The present second embodiment consists of a structural analogue of glutamine where two carbon atoms are replaced with Cu atoms. The chemical formula for this specific compound is $C_3H_{10}Cu_2N_2O_3$.

Figure 13A:
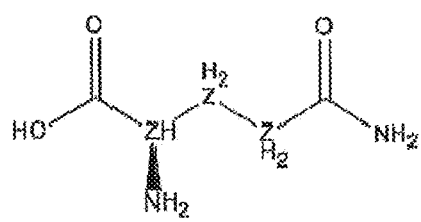
FIG. 13a-13b shows a structural analogue of present invention with 3 carbon replacement.

FIG. 13a, as en example, shows a third embodiment of the present invention, wherein structural analogues of glutamine, more particularly three carbon atoms are replaced with high z elements. Again Z is any high z element as previously defined, such general third embodiment is denoted with the generic chemical formula $C_2H_{10}Z_3N_2O_3$.

Figure 13B:
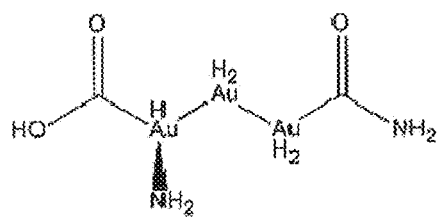

FIG. 13b provides a more specific embodiment of the general embodiment presented in FIG. 13a above. The present third embodiment consists of a structural analogue of glutamine where three carbon atoms are replaced with Au atoms. The chemical formula for this specific compound is $C_2H_{10}Au_3N_2O_3$.

Figure 14:
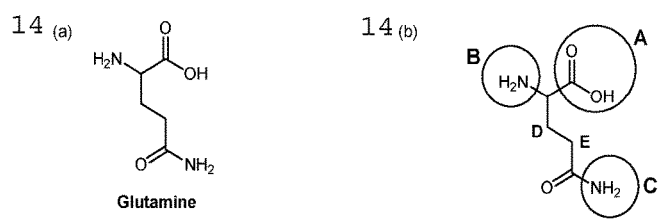
FIG. 14a represents glutamine.
FIG. 14b represents the sites of modification (A, B, C, D or E) of glutamine to which groups with high Z elements can be attached with a ligand.

FIG. 14a represents glutamine. Cancer starvation molecules of the invention provide glutamine molecules having high Z elements attached via a side chain or ligand to the glutamine. The side chain or ligand may be a linker of $(CH_2)n-X$, or $[(CH_2CH_2)_m X]_n$, where X=O, S, or NH, where m and n are integers, and independently range from 1-50, from 1-15 or from 1-10. For example, FIG. 14b represents the sites of modification (A, B, C, D or E) of glutamine to which groups with high Z elements can be attached.

Figure 15:
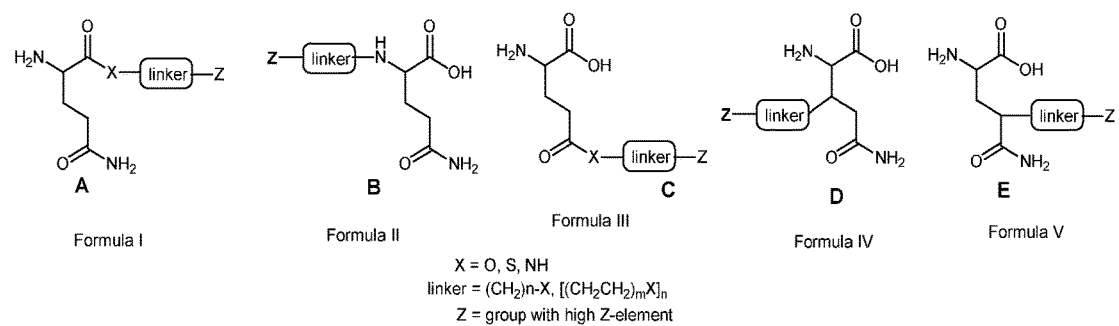
FIG. 15 shows formulas I, II, III, IV and V, showing glutamine, a ligand and the high Z element attached to the glutamine with the ligand.

FIG. 15 shows generic formulas of each of the sites of modification to which structures with Z elements can be attached. In FIG. 15 (c), "Z" represents a group that either is, or contains high Z elements. In the same figure, group "X" can be O, S or NH, to which "Z" can be attached directly or via a "linker." The "linker" should be understood as a short connector consisting of a chain of $CH_2$ groups that can have O, S, or NH groups incorporated.

FIGS. 16-20 represents structures of specific examples of possible modifications on each of the sites A, B, C, D or E. The structures of FIGS. 16-20 should be considered as non limiting examples.

Figure 16:
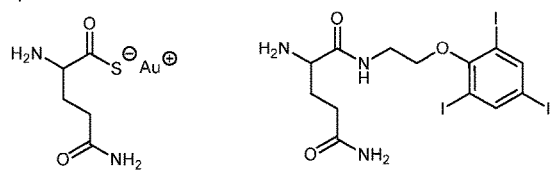
FIG. 16 provides examples of Formula I.

FIG. 16 shows compounds having groups with high Z elements attached to the carboxylic acid group of glutamine.

FIG. 17 shows compounds having groups with high Z elements connected to the amino group of glutamine.

FIG. 18 shows compounds having groups with high Z elements connected to the primary amide group of glutamine.

Figure 19:
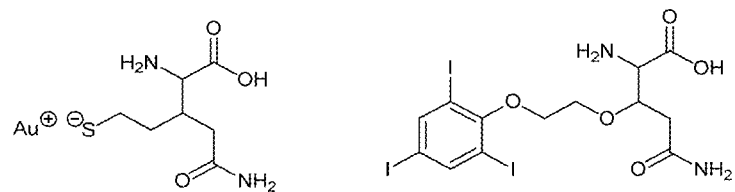
FIG. 19 provides examples of Formula IV.

FIG. 19 shows compounds that maintain the three functional groups of glutamine (A, B and C), and the high Z elements are connected to the side chain β-carbons.

Figure 20:
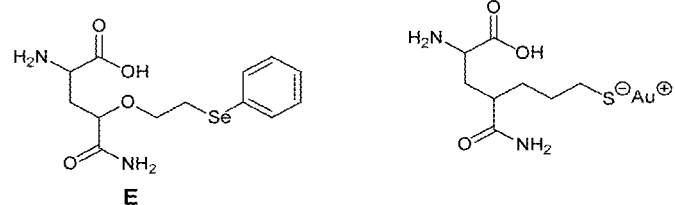
FIG. 20 provides examples of Formula V.

FIG. 20 shows compounds that maintain the three functional groups of glutamine (A, B and C), and the high Z elements are connected to the side chain γ-carbons respectively.

As mentioned, the present compounds are designed to access the mitochondria, wherein the estimated charged particle density from interactions in the area immediately surrounding present invention compound increases dramatically relative to the glutamine it substitutes. For example, as previously mentioned, for a 6 MV photon beam, three gold atoms (Z=79) in such an analogue would yield a factor of 17×3=51:1 higher fluence rate than three carbon atoms they replace. The same replacement would yield a factor of 136:1 and 82:1 for 500 keV photons and an 18 MV beam, respectively.

While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

The invention claimed is:
1. A radiosensitizing containing glutamine-ligand-high Z element compound for treating tumorigenic cells in combination with a high energy radiation,
   wherein the glutamine-ligand-high Z element compound is Formula IA.
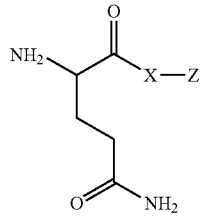
Formula IA
where X = O, S, NH
Z = group with high Z-element gold
* * * * *